(12) United States Patent
Fraser et al.

(10) Patent No.: US 6,592,624 B1
(45) Date of Patent: Jul. 15, 2003

(54) PROSTHETIC IMPLANT ELEMENT

(75) Inventors: Robert D. Fraser, Myrtle Bank (AU); Donald William Howie, Adelaide (AU)

(73) Assignee: DePuy AcroMed, Inc., Raynham, MA (US)

( * ) Notice: Subject to any disclaimer, the term of this patent is extended or adjusted under 35 U.S.C. 154(b) by 0 days.

(21) Appl. No.: 09/714,847

(22) Filed: Nov. 16, 2000

Related U.S. Application Data
(60) Provisional application No. 60/167,272, filed on Nov. 24, 1999.

(51) Int. Cl.⁷ .................................................. A61F 2/44
(52) U.S. Cl. ..................................................... 623/17.16
(58) Field of Search .......................... 623/17.11, 17.13, 623/17.12, 17.15, 17.16; 606/61

(56) References Cited

U.S. PATENT DOCUMENTS

| | | |
|---|---|---|
| 4,272,855 A | 6/1981 | Frey |
| 4,349,921 A | 9/1982 | Kuntz |
| 4,599,086 A | 7/1986 | Doty |
| 4,627,853 A | 12/1986 | Campbell et al. |
| 4,678,470 A | 7/1987 | Nashef et al. |
| 4,685,919 A | 8/1987 | Niwa et al. |
| 4,743,256 A | 5/1988 | Brantigan |
| 4,759,769 A | 7/1988 | Hedman et al. |
| 4,834,757 A | 5/1989 | Brantigan |
| 4,878,915 A | 11/1989 | Brantigan |
| 4,950,296 A | 8/1990 | McIntyre |
| 5,002,576 A * | 3/1991 | Fuhrmann et al. ............ 606/61 |
| 5,053,049 A | 10/1991 | Campbell |
| 5,071,437 A | 12/1991 | Steffee |
| 5,092,893 A | 3/1992 | Smith |
| 5,192,327 A | 3/1993 | Brantigan |
| 5,245,098 A | 9/1993 | Summers et al. |
| 5,246,458 A | 9/1993 | Graham |
| 5,275,954 A | 1/1994 | Wolfinbarger et al. |
| 5,306,303 A | 4/1994 | Lynch |
| 5,306,307 A | 4/1994 | Senter et al. |
| 5,306,308 A | 4/1994 | Gross et al. |

(List continued on next page.)

FOREIGN PATENT DOCUMENTS

| | | |
|---|---|---|
| EP | 0 317 972 | 5/1989 |
| EP | 0 392 076 | 10/1990 |
| EP | 0538183 | 4/1993 |

(List continued on next page.)

OTHER PUBLICATIONS

*Surgical Technique Using FRA Spacer Instruments: Technique Guide*, Synthes Spine, pp. 1–16 (1998).
*Keystone Graft Instruments*, Pamphlet by DePuy Motech, Inc., 6 pages (1998).

*Primary Examiner*—Eduardo C. Robert
(74) *Attorney, Agent, or Firm*—Nutter McClennen & Fish LLP

(57) ABSTRACT

An implantable prosthetic element includes a first end plate and a second end plate, each of which has a bone-facing surface and an opposed mating surface. The bone-facing surfaces of the first end plate and the second end plate each have at least one lobe protruding therefrom. Some or all of the lobes may have a plurality of wedge-like like fins which protrude therefrom. An elastomeric core is interposed between, and attached to, the mating surfaces of the first end plate and the second end plate.

41 Claims, 6 Drawing Sheets

U.S. PATENT DOCUMENTS

| | | | |
|---|---|---|---|
| 5,306,309 | A | 4/1994 | Wagner et al. |
| 5,314,477 | A * | 5/1994 | Marnay ............... 403/112 |
| 5,320,644 | A | 6/1994 | Baumgartner |
| 5,370,697 | A * | 12/1994 | Baumgartner ............ 623/17.15 |
| 5,397,364 | A | 3/1995 | Kozak et al. |
| 5,425,772 | A | 6/1995 | Brantigan |
| 5,429,863 | A | 7/1995 | McMillin |
| 5,443,514 | A | 8/1995 | Steffee |
| 5,443,515 | A | 8/1995 | Cohen et al. |
| 5,458,643 | A | 10/1995 | Oka et al. |
| 5,514,180 | A | 5/1996 | Heggeness et al. |
| 5,522,899 | A | 6/1996 | Michelson |
| 5,534,029 | A * | 7/1996 | Shima ............... 606/61 |
| 5,534,030 | A | 7/1996 | Navarro et al. |
| 5,556,379 | A | 9/1996 | Wolfinbarger |
| 5,571,109 | A | 11/1996 | Bertagnoli |
| 5,607,424 | A | 3/1997 | Tropiano |
| 5,609,635 | A | 3/1997 | Michelson |
| 5,609,637 | A | 3/1997 | Biedermann et al. |
| 5,658,335 | A | 8/1997 | Allen |
| 5,658,337 | A | 8/1997 | Kohrs et al. |
| 5,674,294 | A | 10/1997 | Bainville et al. |
| 5,683,465 | A | 11/1997 | Shinn et al. |
| 5,702,449 | A | 12/1997 | McKay |
| 5,702,450 | A | 12/1997 | Bisserie |
| 5,702,455 | A | 12/1997 | Saggar |
| 5,716,415 | A | 2/1998 | Steffee |
| 5,722,977 | A | 3/1998 | Wilhelmy |
| 5,725,579 | A | 3/1998 | Fages et al. |
| 5,728,159 | A | 3/1998 | Stroever et al. |
| 5,741,253 | A | 4/1998 | Michelson |
| 5,755,798 | A | 5/1998 | Papavero et al. |
| 5,766,252 | A | 6/1998 | Henry et al. |
| 5,766,253 | A | 6/1998 | Brosnahan, III |
| 5,776,196 | A | 7/1998 | Matsuzaki et al. |
| 5,776,199 | A | 7/1998 | Michelson |
| 5,782,832 | A | 7/1998 | Larsen et al. |
| 5,785,710 | A | 7/1998 | Michelson |
| 5,797,871 | A | 8/1998 | Wolfinbarger, Jr. |
| 5,800,550 | A | 9/1998 | Sertich |
| 5,814,084 | A | 9/1998 | Grivas et al. |
| 5,820,581 | A | 10/1998 | Wolfinbarger, Jr. |
| 5,824,094 | A | 10/1998 | Serhan et al. |
| 5,861,041 | A | 1/1999 | Tienboon |
| 5,865,845 | A | 2/1999 | Thalgott |
| 5,865,846 | A | 2/1999 | Bryan et al. |
| 5,888,222 | A | 3/1999 | Coates et al. |
| 5,888,227 | A | 3/1999 | Cottle |
| 5,888,228 | A | 3/1999 | Knothe et al. |
| 5,893,889 | A | 4/1999 | Harrington |
| 5,897,593 | A | 4/1999 | Kohrs et al. |
| 5,904,683 | A | 5/1999 | Pohndorf et al. |
| 5,961,554 | A | 10/1999 | Janson et al. |
| 5,964,807 | A | 10/1999 | Gan et al. |
| 5,972,368 | A | 10/1999 | McKay |
| 5,976,187 | A | 11/1999 | Richelsoph |
| 5,989,289 | A | 11/1999 | Coates et al. |
| 6,019,793 | A | 2/2000 | Perren et al. |
| 6,045,579 | A | 4/2000 | Hochshuler et al. |
| 6,080,193 | A | 6/2000 | Hochshuler et al. |
| 6,093,205 | A | 7/2000 | McLeod et al. |
| 6,096,080 | A | 8/2000 | Nicholson et al. |
| 6,113,638 | A | 9/2000 | Williams et al. |
| 6,120,503 | A | 9/2000 | Michelson |
| 6,143,033 | A | 11/2000 | Paul et al. |
| 6,156,037 | A | 12/2000 | LeHuec et al. |
| 6,168,596 | B1 | 1/2001 | Wellisz |
| 6,176,882 | B1 | 1/2001 | Biedermann et al. |
| 6,258,125 | B1 | 7/2001 | Paul et al. |
| 6,261,586 | B1 | 7/2001 | McKay |
| 6,270,528 | B1 | 8/2001 | McKay |
| 2001/0039456 | A1 | 11/2001 | Boyer, II et al. |
| 2001/0039457 | A1 | 11/2001 | Boyer, II et al. |
| 2001/0039458 | A1 | 11/2001 | Boyer, II et al. |
| 2001/0041941 | A1 | 11/2001 | Boyer, II et al. |
| 2001/0047208 | A1 | 11/2001 | Michelson |
| 2001/0049560 | A1 | 12/2001 | Paul et al. |
| 2001/0056302 | A1 | 12/2001 | Boyer, II et al. |
| 2002/0029084 | A1 | 3/2002 | Paul et al. |
| 2002/0099443 | A1 * | 7/2002 | Messerli et al. ......... 623/17.11 |

FOREIGN PATENT DOCUMENTS

| | | |
|---|---|---|
| EP | 0 610 837 | 8/1994 |
| FR | 2703580 | 10/1994 |
| FR | 2 775 587 | 9/1999 |
| WO | 9426213 | 11/1994 |
| WO | 9508306 | 3/1995 |
| WO | 9817209 | 4/1998 |
| WO | 9855052 | 12/1998 |
| WO | 9856319 | 12/1998 |
| WO | 9856433 | 12/1998 |
| WO | WO 99/30651 | 6/1999 |
| WO | WO 01//49220 | 7/2001 |
| WO | WO 01/62191 | 8/2001 |
| WO | WO 01/66048 | 9/2001 |
| WO | WO 01/70137 | 9/2001 |
| WO | WO 01/78798 | 10/2001 |

\* cited by examiner

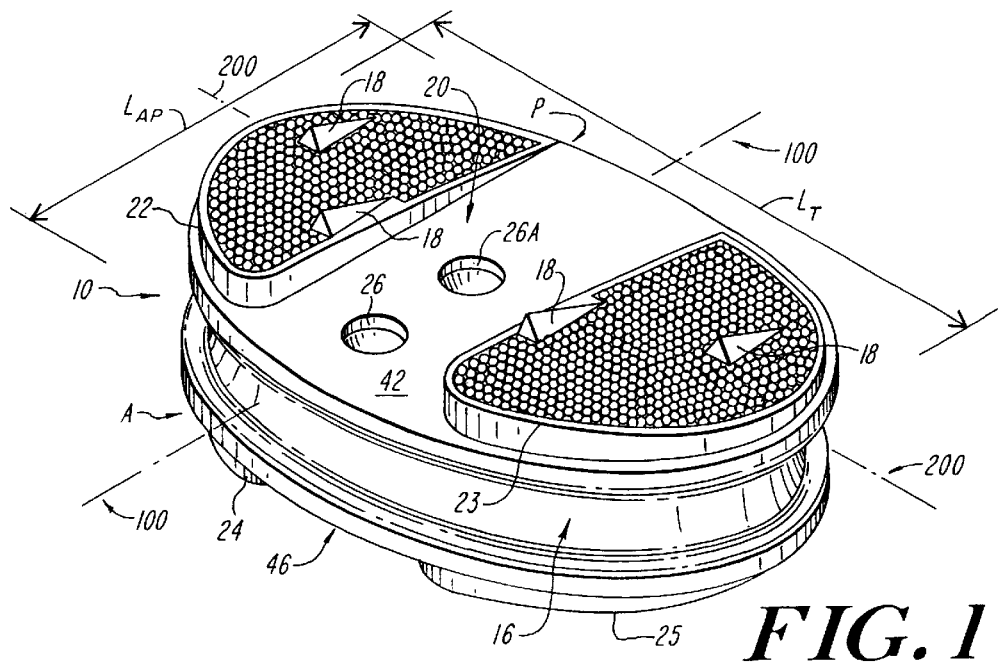
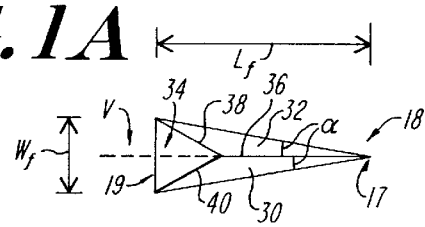
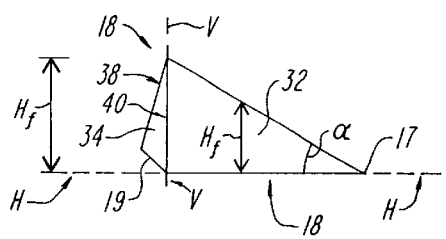
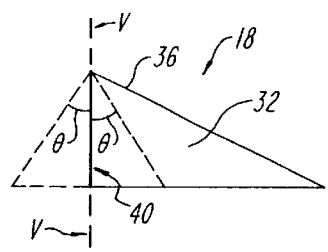
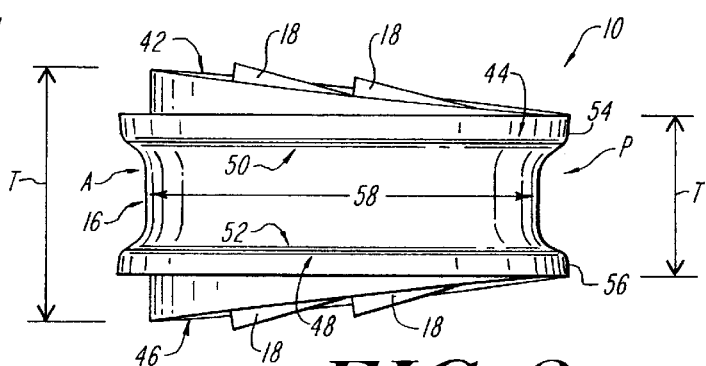

PROSTHETIC IMPLANT ELEMENT

CROSS-REFERENCE TO RELATED APPLICATIONS

This application is based on and claims priority from U.S. patent application Ser. No. 60/167,272, filed Nov. 24, 1999.

STATEMENT REGARDING FEDERALLY SPONSORED RESEARCH

Not Applicable.

FIELD OF THE INVENTION

The present invention relates to medical devices, and particularly to prosthetic implant components, and more particularly to an implantable artificial spinal disc.

BACKGROUND OF THE INVENTION

Advancing age, as well as injuries, can lead to changes in the various bones, discs, joints, and ligaments of the body. Such changes and injuries often manifest themselves in the form of damage or degeneration of a spinal disc, the result of which is mild to severe chronic back pain. Under certain circumstances, this pain can be lessened or completely alleviated by removal of the damaged or degenerated spinal disc, followed by the implantation of an artificial intervertebral disc.

Many artificial intervertebral discs are known, such as those disclosed in U.S. Pat. Nos. 5,893,889 to Harrington, U.S. Pat. No. 5,683,465 to Shinn et al.5,674,294 to Bainville et al., U.S. Pat. No. 5,458,643 to Oka et al., U.S. Pat. No. 5,306,309 to Wagner et al., U.S. Pat. No. 5,246,458 to Graham, and U.S. Pat. No. 4,759,769 to Hedman. There remains a need, however, to substantially simulate a healthy spinal disc, while still allowing for ease of insertion and/or removal of the prosthetic device, and while providing adequate protection against expulsion of the implanted prosthetic disc. Thus, it remains a goal in the art to produce a prosthetic device, such as an artificial intervertebral disc, that possesses these properties.

SUMMARY OF THE INVENTION

The present invention provides an implantable prosthetic element. Although the invention is primarily shown and described as an artificial disc prosthesis, it is understood that the invention has other applications as well, such as for use as an ankle or heel prosthesis.

The implantable prosthetic element has a first end plate and a second end plate, each of which has a bone-facing surface and an opposed mating surface. The bone-facing surfaces of the first end plate and the second end plate each have a plurality of lobes protruding therefrom. An elastomeric core is interposed between and attached to the mating surfaces of the first end plate and the second end plate. The prosthetic element is constructed such that the thickness is greater at the anterior side than at the posterior side. As a result, the lobe surface is generally oriented at an angle, sloping from the anterior to the posterior side.

Some or all of the plurality of lobes include one or more wedge-like fins which protrude therefrom. The lobes may also include a plurality of surface features that promote osteo-integration.

In one embodiment of the present invention, the first end plate and the second end plate each contain two lobes, with a slot separating the two lobes of each end plate. Each slot may optionally include one or more recesses to facilitate insertion and/or extraction of the element from its implantation site.

BRIEF DESCRIPTION OF THE DRAWINGS

The invention will be more fully understood from the following detailed description taken in conjunction with the accompanying drawings, in which:

FIG. 1 is a perspective view of an implantable prosthetic element in accordance with the present invention;

FIG. 1A is a top, plan view of a wedge-like fin of the element of FIG. 1;

FIG. 1B is a perspective view of a wedge-like fin of the element of FIG. 1;

FIG. 1C is a side view of a wedge-like fin of the element of FIG. 1C;

FIG. 2 is a side, elevational view of the implantable prosthetic element of FIG. 1;

DETAILED DESCRIPTION OF THE DRAWINGS

Figure 3:
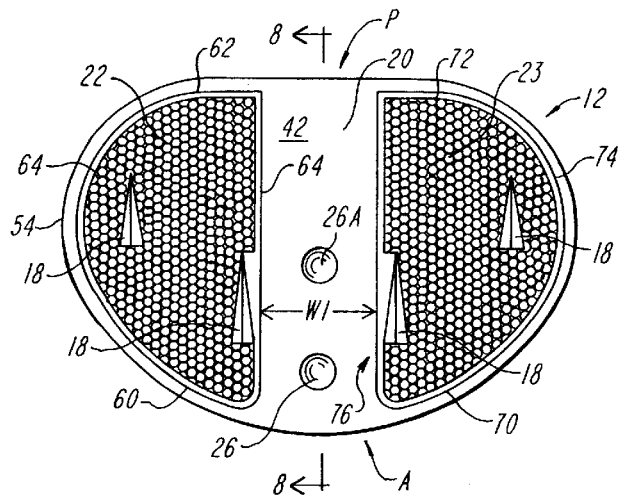
FIG. 3 is a plan view of the bone-facing surface of the first end plate of the implantable prosthetic element of FIG. 1.

Referring initially to FIGS. 1, 1A, 1B, 2, 3, 4 and 5, an implantable prosthetic element 10 is shown. The element 10 has a first end plate 12 and a second end plate 14. The first end plate 12 has a bone-facing surface 42 and an opposed mating surface 44, and the second end plate 14 has a bone-facing surface 46 and an opposed mating surface 48. An elastomeric core 16 is interposed between and attached to the mating surfaces 44, 46 of the first and second end plates 12, 14.

Figure 6:
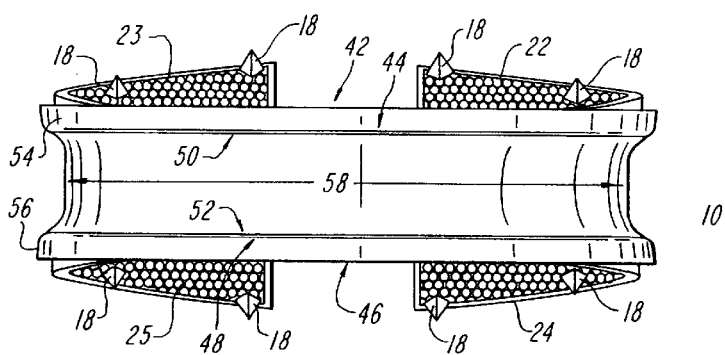
FIG. 6 is a front, elevational view of the implantable prosthetic element of FIG. 1.
Figure 7:
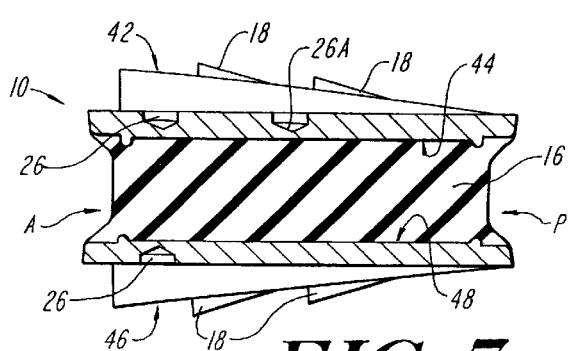
FIG. 7 is a sectional view along line 7—7 of the implantable prosthetic element of FIG. 4.
Figure 8:
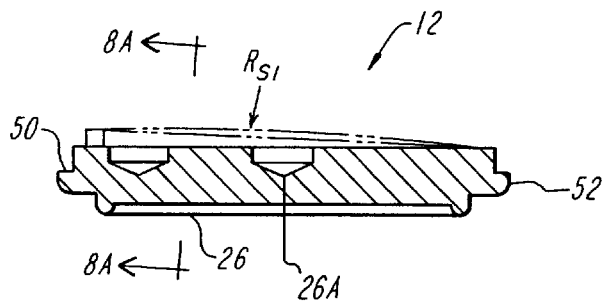
FIG. 8 is a sectional view along line 8—8 of the implantable prosthetic element of FIG. 3.
Figure 8A:
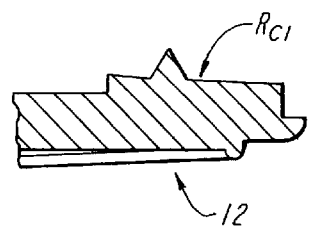
FIG. 8A is a sectional view along line 8A—8A of FIG. 8.

The first and second end plates 12, 14 include bone-facing surfaces 42, 46. As shown in FIGS. 1 and 2–4, the bone facing surface 42 of the first end plate 12 includes adjacent lobes 22, 23 separated by at least one slot 20. The slot 20 may include one or more extraction recesses 26, formed as blind bores in the slot surface. A further surface feature 26A may also be formed on the surface of slot 20 of the bone-facing surface 42 of the first end plate 12, serving as a visual key to indicate the top or superior surface of element 10. Surface feature 26A may be in the form of a recess or a protrusion. Similarly, as shown in FIGS. 5–7, the second end plate 14 has a bone-facing surface 46 with adjacent lobes 24, 25 that are separated by a slot 21. Either or both of the bone-facing surfaces 42, 46 of the first end plate 12 and the second end plate 14 of the element 10 can include one or more bone-penetrating, wedge-like fins 18 protruding therefrom.

One of ordinary skill in the art will appreciate that bone-facing surfaces 42, 46 may include only a single lobe, or more than two lobes. If only a single lobe is present, there need not be a slot. If more than two lobes are present, more than one slot may exist.

In the illustrated embodiment, each lobe 22, 23, 24, 25 is elevated above the surfaces of slots 20, 21. FIGS. 2 and 7 illustrate that the dimensions and geometry of the end plates 12, 14 and the lobes 22, 23, 24, 25 cause the overall thickness (T) of the element 10 to taper from the anterior face (A) to the posterior face (P) at an angle in the range of about 2° to 35°, and more preferably about 5° to 15°. Thus, the thickness (T) of the element 10 is greatest when measured between the anterior portions of the lobes, and least when measured between the posterior portions of the lobes. The thickness T of element 10 at the anterior side is in the range of about 5 to 21 mm, while the thickness T at the posterior side is in the range of about 1 mm to 15 mm.

Element 10 has an anterior side (A) and a posterior side (P), with an anterior-posterior (A-P) axis 100 extending therebetween. A transverse axis 200 extends through element 10 perpendicular to the A-P axis 100. As shown in FIGS. 1, 2, 4, 6 and 7, each of the first and second bone-facing surfaces 42, 46 includes a peripheral flange 54, 56 which extends beyond the perimeter of the lobes 22, 23, 24, 25. As shown in the top plan views of FIGS. 3, 3A, 3B, 5 and 5A, the peripheral flanges 54, 56 of the bone-facing surfaces 42, 46 are similarly sized and shaped.

As noted above, element 10 may contain bone-penetrating, wedge-like fins 18 to enhance secure implantation of the element 10 at the desired location, and to prevent the expulsion of the element from its implantation location. The fins 18 may vary in shape, number, and in their placement on either of both of the end plates 12, 14.

As illustrated, exemplary fins 18 are elongated, with a length ($L_f$) that extends from a leading end 17 of each fin to a trailing end 19 of each fin such that the length of each fin is greater than a width ($W_f$) of each fin. Each fin 18 also has a height ($H_f$) that increases from the leading end 17 of the fin to the trailing end 19 of each fin. In one embodiment, the height $H_f$ of each fin 18 is in the range of about 0.1 mm to 5.0 mm, and more preferably in the range of about 1.0 mm to 2.0 mm. at the trailing end 19 of the fin. Generally, the length $L_f$ of each fin is in the range of about 1 mm to 30 mm, and more preferably about 3 mm to 9 mm, and the width $W_f$ of each fin, at its widest point, is in the range of about 1 mm to 4 mm.

Due to the increasing height of each fin from leading end 17 to trailing end 19, the crest 36 of each fin extends from the leading end 17 of the fin to the trailing end 19 of the fin at an angle of extension ($\alpha$). The angle of extension a may be in the range of about 5° to 85° with respect to a horizontal reference (H).

As shown in FIGS. 1 and 1A–1C, each fin 18 may have a substantially triangular profile, with supporting legs 38, 40 that form first and second bone-contacting surfaces 30, 32 that diverge from the crest 36. The supporting legs 38, 40 extend from the crest 36 to the bone-facing, superior surface 42, 46 of an end plate 12, 14 at an angle ($\theta$) in the range of about 5° to 85° from a vertical reference (V) as shown in FIG. 1C.

In one embodiment, the trailing end 19 of each fin 18 includes an end face 34 that extends from the crest 36 to the bone-facing surface 42, 46 of end plates 12, 14. Preferably, the end face 34 is generally anterior-facing. The end face 34 is shown in FIG. 1B as being substantially perpendicular to a horizontal reference (H) and substantially parallel to a vertical reference (V). End face 34, however, may also be non-parallel to the vertical reference (V), such as, for example, undercut or overcut with respect to the vertical reference (V) as shown by dashed lines in FIG. 1C.

Although fins 18 are described and illustrated as having a substantially wedge-like shape with a triangular profile, one of ordinary skill in the art will appreciate that other shapes may be used as well. It is also understood that the dimensions, i.e., height, length, and width of the fins may vary, as may the overall geometry of the fins.

With respect to the number of fins 18, there should generally be at least one fin protruding from each of the bone-facing surface 42 of the first end plate 12 and the bone-facing surface 46 of the second end plate 14. Preferably, the number of fins on each of the bone-facing surface 42 of the first end plate 12 and the bone-facing surface of the second end plate 14 is identical. In exemplary embodiments of the present invention, the number of fins protruding from each bone-facing surface 42, 46 is four (see FIGS. 3 and 5) and six (see FIGS. 3A, 3B and 5A). One of ordinary skill in the art, however, will understand that the number of fins 18 protruding from each bone-facing surface 42, 46 need not be identical. And, the number of fins 18 protruding from each bone-facing, superior surface 42, 46 may be greater than six or less than four.

Figure 3B:
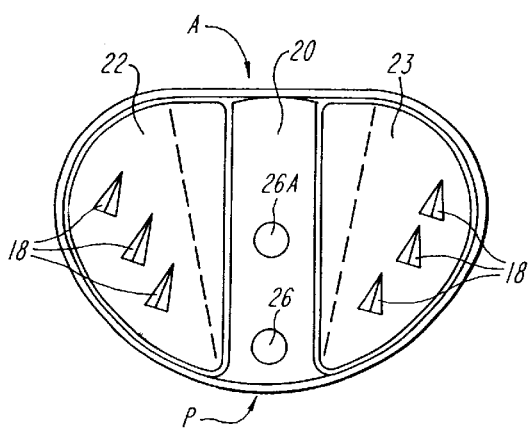
FIG. 3B is a plan view of another embodiment of the bone-facing surface of the first end plate of the implantable prosthetic element of FIG. 1.
Figure 3A:
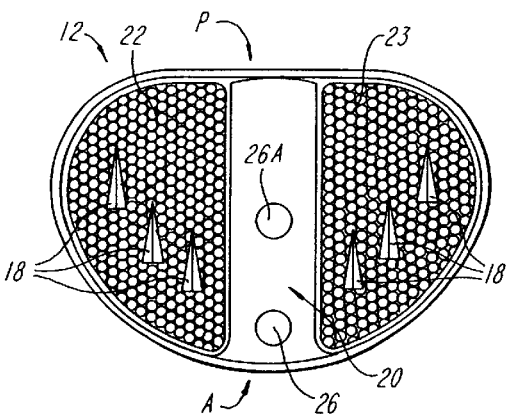
FIG. 3A is a plan view of an alternate embodiment of the bone-facing surface of the first end plate of the implantable prosthetic element of FIG. 1.

Each fin 18 should be arranged on bone-facing surfaces 42, 46 such that the crests 36 of each fin are substantially parallel to each other. In one embodiment, shown in FIGS. 3, 3A, 5 and 5A, the fins 18 are arranged such that crests 36 are substantially parallel to the anterior-posterior axis 100 of the element. In other embodiments, for example FIG. 3B, the fins 18 may be oriented such that crests 36 extend at an angle with respect to the anterior-posterior (A-P) axis 100. One of ordinary skill in the art will readily appreciate that the fins 18 should be oriented so that the crests 36 are parallel with the desired angle of insertion to be used by a surgeon during surgical installation of element 10. For example, if element 10 is to be used as an artificial intervertebral disc, the crests 36 of the fins 18 will be parallel to the A-P axis 100 if an anterior surgical approach is to be used. Alternatively, the crests 36 of the fins will be angled as shown in FIG. 3B if an anterior-lateral approach is to be used. One of ordinary skill in the art can readily determine an appropriate angular orientation of fins 18.

The fins 18 may be arranged on the bone-facing surfaces 42, 46 in a variety of patterns, which will be readily apparent to one of ordinary skill in the art. Exemplary patterns are illustrated in FIGS. 1, 3, 3A, 3B, 5 and 5A.

One of ordinary skill in the art will appreciate that although fins 18 exist in a currently preferred embodiment of the invention, an implantable prosthetic element may be constructed without fins.

As shown in FIGS. 1, 2, 4, 6 and 7, the elastomeric core 16 is interposed between and attached to the first end plate 12 and the second end plate 14 as disclosed in U.S. Pat. No. 5,824,094 to Serhan, which is expressly incorporated by reference herein. The core 16 has a superior core surface 50, an inferior core surface 52 and a central peripheral portion 58.

As noted above, peripheral. flanges 54, 56 form the perimeter or widest portions of the first and second end plates 12, 14. The perimeter of the core peripheral portion 58 is generally about equal to the perimeter of the first and second peripheral flanged portions 54, 56 at the superior and inferior core surfaces 50, 52. However, the core 16 is preferably sub-flush with respect to the end plates 12, 14 such that the perimeter of the core peripheral portion 58 tapers inward to a center portion from both the superior core surface 50 and the inferior core surface 52. Thus, the perimeter of the central peripheral portion 58 of core 16 is generally less than the perimeter of the superior and inferior core surfaces 50, 52 of core by an amount in the range of about 0.1 mm to 4 mm. One of ordinary skill in the art will understand, however, that alternate geometries may be utilized as well. For example, the peripheral flanges 54, 56 may be different sizes, and the perimeter of the core 16 need not be sub-flush with respect to end plates 12, 14.

The lobes 22, 23, 24, 25 may have various shapes and dimensions in accordance with the present invention. Each lobe has an anterior portion, a posterior portion and first and second side portions. As shown in FIG. 3, lobe 22 has an anterior portion 60, a posterior portion 62, a first side portion 64, and a second side portion 66, while lobe 23 has an anterior portion 70, a posterior portion 72, a first side portion 74, and a second side portion 76. As shown in FIG. 5, lobe 24 has an anterior portion 80, a posterior portion, 82, a first side portion 84, and a second side portion 86, while lobe 23 has an anterior portion 90, a posterior portion 92, a first side portion 94, and a second side portion 96.

Lobes 22, 23, 24, 25 have heights that are defined as the distance each lobe protrudes from the surface of slots 20, 21 of end plates 12, 14. In an exemplary embodiment of the present invention, the orientation of the bone-facing surfaces 42, 46, which are generally angled from the anterior side to the posterior side with respect to horizontal, has the effect that the height of each of lobes 22, 23, 24, 25 decreases from their anterior portions 60, 70, 80, 90 to their posterior portions 62, 72, 82, 92. In general, the height of each lobe 22, 23, 24, 25 is in the range of about 1 mm to 6 mm at the anterior side to about 0.1 mm to 1.0 mm at the posterior side In an exemplary embodiment of the present invention, each of lobes 22, 23, 24, 25 is coated, plated or otherwise treated as is generally known in the art to provide a surface with features that promote osteo-integration. The osteo-integration enhancing surface features may be provided by, for example, applying a porous or beaded coating of a biocompatible material (e.g., titanium), a mesh layer, or a hydroxy apatite coating. One of ordinary skill in the art will appreciate that all or part of lobes 22, 23, 24, 25 may be treated to provide osteo-integration. It is also understood that portions of the bone-facing surfaces 42, 46, in addition to or in lieu of the lobes, may be treated to provide osteo-integration enhancing surface features.

As noted above, the slots 20, 21 represent unlobed areas of the bone-facing surfaces 42, 46 of the end plates 12, 14. In one embodiment, the widths (W1, W2) of slots 20, 21 may be substantially constant along the entire anterior-posterior length ($L_{AP}$) of the element 10. The widths (W1, W2) should be sufficient to enable an installation tool (not shown) to grasp the element 10, and position the element in its to implantation site. The widths (W1, W2) of slots 20, 21 generally are equal.

Figure 5:
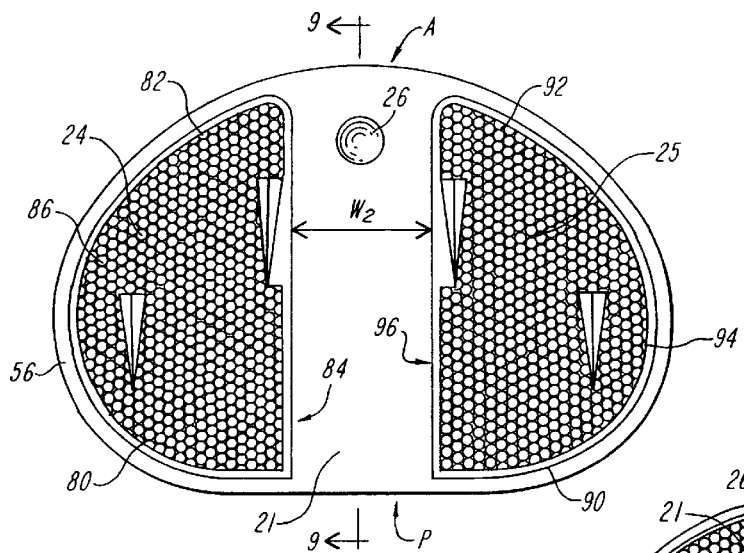
FIG. 5 is a plan view of the bone-facing surface of the second end plate of the implantable prosthetic element of FIG. 1.
Figure 5A:
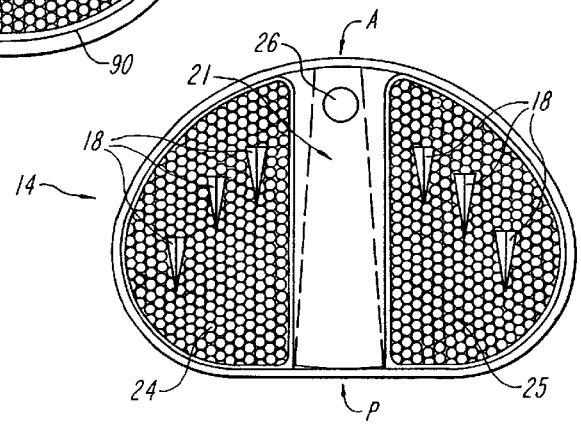
FIG. 5A is a plan view of an alternate embodiment of the bone-facing surface of the second end plate of the implantable prosthetic element of FIG. 1.

In FIGS. 1, 3, 5 and 5A widths W1 And W2 are shown as being identical and substantially constant and oriented to be parallel to the anterior-posterior axis 100 of the element 10. This design is preferred when the element 10 is to be inserted via an anterior approach. Alternatively, the slots 20, 21 may be configured in other ways to accommodate an anterior-lateral insertion technique. For example, the width (W1, W2) of slots 20, 21 can increase from the anterior side to the posterior side, or from the posterior side to the anterior side, as shown in FIG. 3B by dashed lines. FIG. 5A illustrates another alternative in which the slots 20, 21 (shown by dashed lines) are widest at the anterior side and narrowest at the posterior side of the element 10. In either embodiment, the width (W1, W2) is generally in the range of about 4 mm to 14 mm.

FIGS. 8, 8A, 9, and 9A further illustrate the geometry of lobes 22, 23, 24, and 25. As noted above, the bone-facing surfaces 42, 46 of end plates 12, 14 are substantially angled, sloping from the anterior to the posterior sides of the element 10. In addition to being mounted upon this canted surface of the end plates 12, 14, the lobes 22, 23, 24, and 25 each have substantially dome-like profiles, causing them to be curved in both the sagittal and coronal planes.

Figure 4:
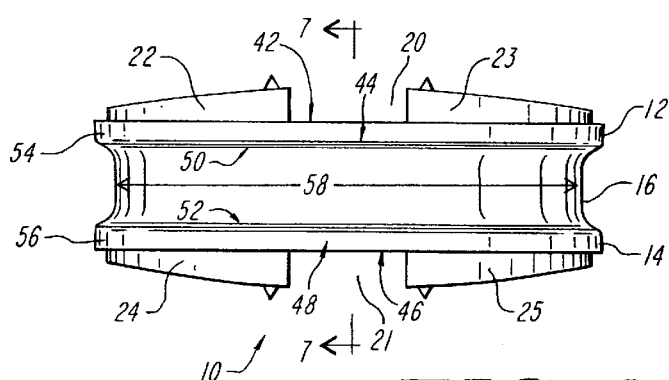
FIG. 4 is a front, elevational view of the implantable prosthetic element of FIG. 1.
Figure 9:
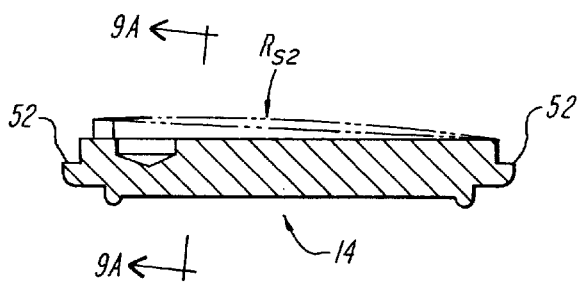
FIG. 9 is a sectional view along line 9—9 of the implantable prosthetic element of FIG. 5.
Figure 9A:
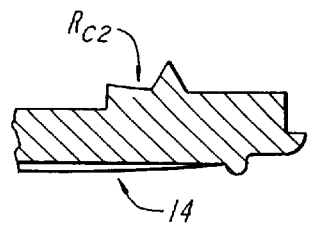
FIG. 9A is a sectional view along line 9A—9A of FIG. 9.

FIGS. 4, 6, 8A and 9A illustrate the radius of curvature in the coronal plane of lobes 22, 23, 24, and 25 of end plates 12, 14. FIGS. 4 and 6 illustrate that the curve of the lobes 22, 23, 24, and 25 in the coronal plane is truncated by slots 20, 21. The radius of curvature of lobes 22 and 23 of end plate 12 ($R_{C1}$) is in the range of about 50 mm to 350 mm, and is preferably in the range of about 100 mm to 200 mm. Most preferably, $R_{C1}$, is about 150 mm. The radius of curvature of lobes 24 and 25 of end plate 14 ($R_{C2}$) is generally flatter than $R_{C1}$. As shown in FIG. 9A, $R_{C2}$ may be in the range of about 50 mm to 350 mm, and more preferably is in the range of about 200 mm to 300 mm. Most preferably, $R_{C2}$ is about 265 mm.

FIGS. 2, 7, 8 and 9 illustrate the radius of curvature in the sagittal plane of lobes 22, 23, 24, and 25 of end plates 12, 14. As illustrated, the lobes have a substantially dome-like profile. The radius of curvature of the lobes 22, 23 of end plate 12 ($R_{S1}$) and the radius of curvatures of the lobes 24, 25 of the end plate 14 ($R_{S2}$) are generally equal. The value of $R_{S1}$, and $R_{S2}$ may be in the range of about 50 mm to 350 mm, and preferably about 100 mm to 200 mm. Most preferably, $R_{S1}$ and $R_{S2}$ are about 140 mm.

Figure 10:
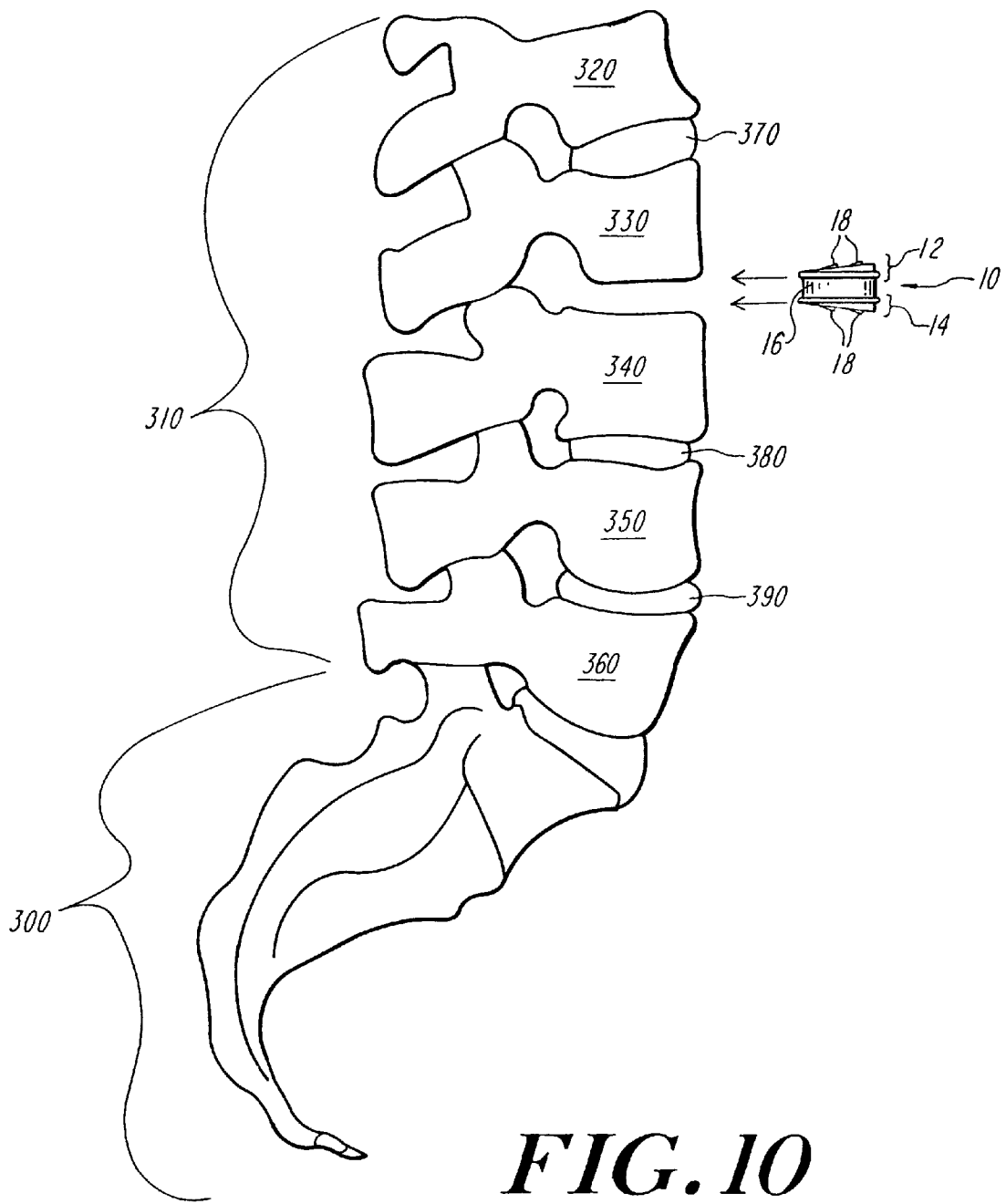
FIG. 10 is a schematic view of the implantable prosthetic element of FIG. 1 immediately prior to its insertion between spinal vertebrae.
Figure 11:
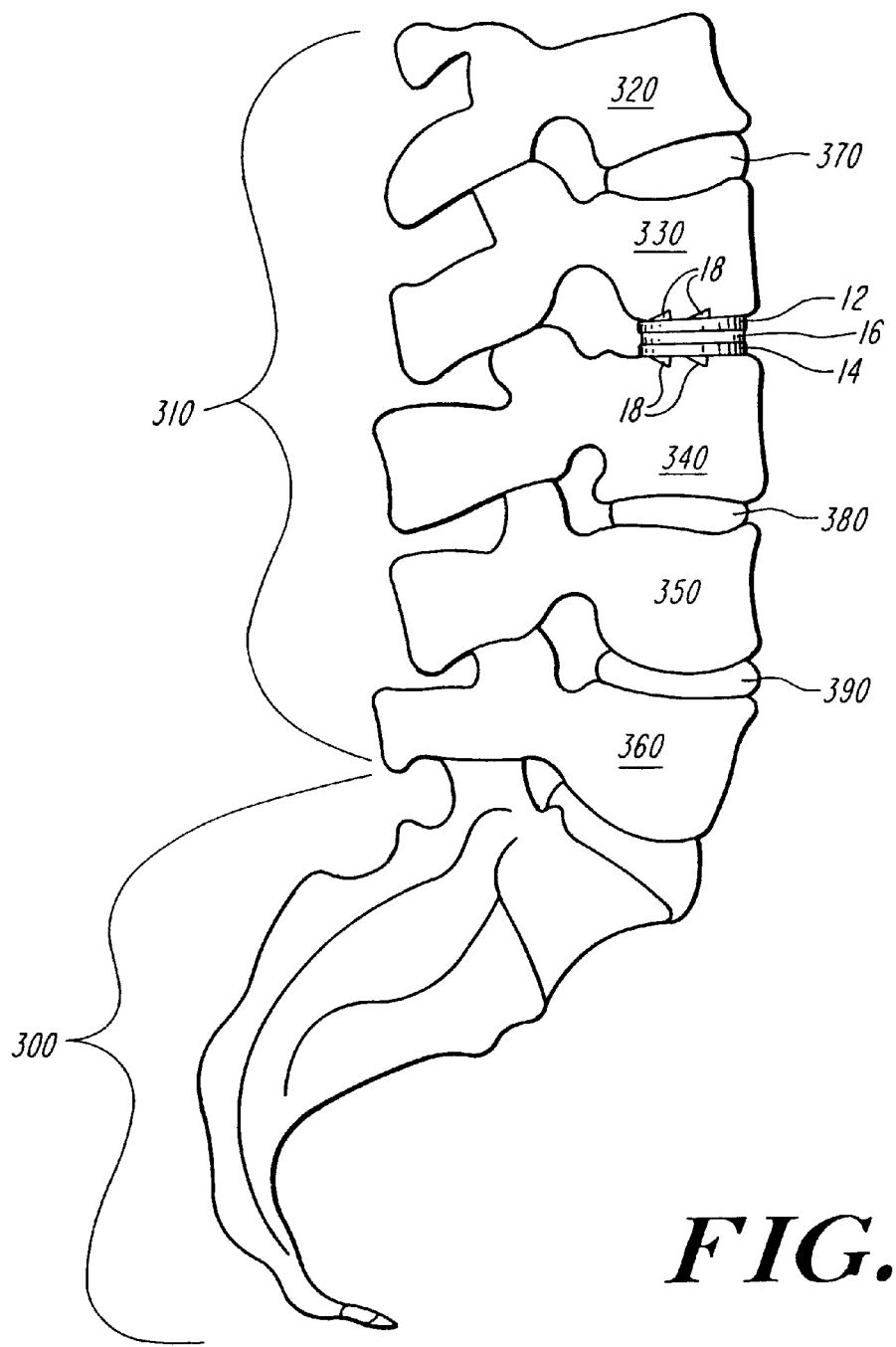
FIG. 11 is a schematic view of the implantable prosthetic element of FIG. 1 following its insertion between spinal vertebrae.

Referring now to FIGS. 10 and 11, the element 10 of the present invention is shown immediately prior to (see FIG. 10) and following (see FIG. 11) its implantation. Specifically, FIGS. 10 and 11 depict the sacrum 300 and lumbar portion 310 of the spine, and the five lumbar vertebrae 320, 330, 340, 350, 360. Natural discs 370, 380, 390 are located between vertebrae 320 and 330, 340 and 350, and 350 and 360. The natural disc that was present between vertebrae 330 and 340 has been removed and will be replaced by element 10. One of ordinary skill in the art will recognize that the element 10 may replace discs 370, 380 or 390, and may also replace discs located between thoracic vertebrae (not shown) or cervical vertebrae (not shown) of the spine.

The element 10 is implanted with an insertion tool (not shown) between lumbar vertebrae 330, 340 using an anterior approach as indicated by the arrows in FIG. 10. Specifically, the posterior portions 62, 72, 82, 92 of lobes 22, 23, 24, 25 of the end plates 12, 14 are inserted prior to the anterior portions 60, 70, 80, 90 of the lobes. One of ordinary skill in the art will recognize, however, that the element 10 may be inserted in other directions including, but not limited to, in an anterior-lateral direction. Once implanted (see FIG. 11), the first and second bone-contacting surfaces 30, 32 of each fin 18 of the first end plate 12 penetrate vertebra 330, while the first and second bone-contacting surfaces 30, 32 of the second end plate 14 penetrate vertebra 340.

The element 10 may be constructed according to the present invention in a variety of sizes depending upon factors such as patient size and intended location in the spine. Generally, the element 10 has an anterior (A) to posterior (P) length ($L_{AP}$) in the range of about 5 mm to 40 mm, and a transverse length ($L_T$) in the range of about 10 mm to 60 mm. Exemplary elements 10 may have dimensions ($L_{AP} \times L_T$) of 34 mm×46 mm, 31.5 mm×43 mm, 29 mm×40 mm, 26.5 mm×37 mm, and 24 mm×34 mm. The element also has a posterior (P) aspect thickness that may be in the range of about 1 mm to 15 mm, and an anterior (A) aspect thickness that may be in the range of about 5 mm to 21 mm.

The first end plate 12, second end plate 14, fins 18 and core 16 of the element 10 may be made of a variety of materials well known to those having ordinary skill in the art. The first and second end plates 12, 14 and the fins 18 are preferably made of the same material, such as a biocompatible metal or biocompatible metal-based alloy. An exemplary metal is titanium, while exemplary alloys include, but are not limited to, stainless steel (e.g., 316 LVM stainless steel), a titanium-vanadium-aluminum alloy (e.g., an alloy having about 90% by weight titanium, about 6% by weight aluminum, and about 4% by weight vanadium), a cobalt-chromium alloy, a cobalt-chromium-molybdenum alloy and a cobalt-nickel-chromium-molybdenum alloy. The end plates 12, 14 may also be made of other biocompatible materials including, but not limited to, a composite plastic material.

The core 16 may be made of any material that simulates the characteristics of a natural disc. Exemplary materials include, but are not limited to, elastomeric materials, a polyolefin rubber (such as a non-conjugated diolefin as described in U.S. Pat. No. 5,245,098 to Summers et al., which is expressly incorporated by reference herein), or a carbon black reinforced polyolefin rubber. The hardness of the elastomeric core 16 should be between 56–72 shore A durometer, while the ultimate tensile strength of the core should be greater than 1600 psi. The core should have an ultimate elongation greater than 300% using the ASTM D412-87 testing method, and a tear resistance greater than 100 psi using the ASTM D624-86 testing method.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable prosthetic element, comprising:
   a first end plate having a first bone-facing surface and an opposed mating surface, the first bone-facing surface having at least one lobe protruding therefrom;
   a second end plate having a second bone-facing surface and an opposed mating surface, the second bone-facing surface having at least one lobe protruding therefrom; and
   a core interposed between and attached to the mating surfaces of the first end plate and the second end plate, wherein the bone-facing surface of at least one of the first end plate and the second end plate includes at least one discrete bone-penetrating fin protruding therefrom.

2. The element of claim 1, wherein each of the at least one bone-penetrating fins is elongated, having a length greater than a width, wherein the length extends from a leading end of each fin to a trailing end of each fin, and wherein each fin has a height that increases from the leading end to the trailing end.

3. The element of claim 2, wherein the leading end of each of the at least one fins is substantially flush with the bone-facing surface of the end plate, and the trailing end of each of the at least one fins is raised from the bone facing surface by a height in the range of about 0.1 mm to 5.0 mm.

4. The element of claim 2, wherein the length of each of the at least one fins is in the range of about 1 mm to 30 mm.

5. The element of claim 2, wherein each of the at least one fins has a crest extending from the leading end to the trailing end at an angle with respect to horizontal in the range of about 5° to 85°.

6. The element of claim 5, wherein the crest is oriented so as to be parallel to an anterior-posterior axis of the element.

7. The element of claim 5, wherein the crest is oriented at an angle with respect to an anterior-posterior axis of the element.

8. The element of claim 2, wherein each of the at least one fins has a substantially triangular profile forming first and second bone-contacting surfaces, with supporting legs diverging away from a crest at opposite sides thereof.

9. The element of claim 8, wherein the trailing end of each of the at least one fins includes an end face that extends from the crest to the bone-facing surface of the end plate.

10. The element of claim 9, wherein the end face is oriented at about 90° with respect to horizontal.

11. The element of claim 9, wherein the end face is undercut with respect to vertical.

12. The element of claim 9, wherein the end face is overcut with respect to vertical.

13. The element of claim 1, wherein a plurality of fins are provided on each of the first end plate and the second end plate.

14. The element of claim 13, wherein the number of fins that protrude from the first end plate is equal to the number of fins that protrude from the second end plate.

15. The element of claim 1, wherein at least one fin protrudes from each lobe of the first and second end plates.

16. The element of claim 1, wherein at least two fins protrude from each of the first and second end plates.

17. The element of claim 1, wherein the bone facing surface of the first end plate has a first lobe and a second lobe and the bone facing surface of the second end plate has a third lobe and a fourth lobe, and wherein a first slot is defined between the first lobe and the second lobe, and a second slot is defined between the third lobe and the fourth lobe.

18. The element of claim 17, wherein the first and second slots each have a constant width from an anterior end of the element to a posterior end of the element.

19. The element of claim 18, wherein each of the first and second slots contain at least one extraction recess.

20. The element of claim 17, wherein the first and second slots each have a width that decreases from an anterior side of the element to a posterior side of the element.

21. The element of claim 17, wherein the first and second slots each have a width that increases from an anterior side of the element to a posterior side of the element.

22. The element of claim 17, wherein each of the at least one first and second lobes has a height, an anterior portion, a posterior portion, and first and second side portions, and wherein the height of each lobe decreases from the anterior portion to the posterior portion and increases from the first side portion to the second side portion.

23. The element of claim 1, wherein each of the at least one of the lobes formed on the first end plate and the second end plate include osteo-integration enhancing surface features.

24. The element of claim 23, wherein the osteo-integration enhancing surface features are selected from the group consisting of a porous coating, a beaded coating, a mesh layer and a hydroxy apatite coating.

25. The element of claim 1, wherein the element has a posterior aspect thickness in the range of about 1 millimeter to 15 millimeters.

26. The element of claim 1, wherein the element has an anterior-posterior length in the range of about 5 millimeters to 40 millimeters.

27. The element of claim 1, wherein the element has a transverse length in the range of about 10 millimeters to 60 millimeters.

28. The element of claim 1, wherein the first end plate and the second end plate each have a sagittal radius in the range of 50 millimeters to 350 millimeters and a coronal radius in the range of 50 millimeters to 350 millimeters.

29. The element of claim 1, wherein the core is formed of an elastomeric material.

30. The element of claim 1, wherein the core is formed of a material selected from the group consisting of an elastomeric material and a polyolefin rubber.

31. The element of claim 30, wherein the polyolefin rubber is carbon black reinforced.

32. An implantable prosthetic element, comprising:

a first end plate having a first bone-facing surface and an opposed first mating surface;

a second end plate having a second bone-facing surface and an opposed second mating surface; and an elastomeric core interposed between and attached to the inferior mating surfaces of the first end plate and the second end plate;

wherein the bone-facing surface of at least one of the first and second end plates includes at least one slot formed therein.

33. The element of claim 32, wherein the first bone facing surface of the first end plate has two adjacent lobes protruding therefrom.

34. The element of claim 33, wherein the slot separates the two lobes.

35. The element of claim 32, wherein the second bone facing surface of the second end plate has two adjacent lobes protruding therefrom.

36. The element of claim 35, wherein the slot separates the two lobes.

37. The element of claim 32, further comprising at least one bone-penetrating fin formed on the bone-facing surfaces of the first and second end plates.

38. The element of claim 37, wherein each of the at least one bone-penetrating fins has a height that increases from a leading end of the fin to a trailing end of the fin.

39. The element of claim 32, wherein the core is formed of an elastomeric material.

40. The element of claim 32, wherein the core is formed of a material selected from the group consisting of an elastomeric material and a polyolefin rubber.

41. The element of claim 40, wherein the polyolefin rubber is carbon black reinforced.

* * * * *